United States Patent [19]

Humphrey

[11] Patent Number: 4,968,673

[45] Date of Patent: Nov. 6, 1990

[54] USE OF A THROMBOXANE RECEPTOR ANTAGONIST IN RENAL DISEASES AND DYSFUNCTION

[75] Inventor: Patrick P. A. Humphrey, Wrestlingworth, England

[73] Assignee: Glaxo Group Limited, London, England

[21] Appl. No.: 368,587

[22] Filed: Jun. 20, 1989

[30] Foreign Application Priority Data

Jun. 21, 1988 [GB] United Kingdom ............... 8814726

[51] Int. Cl.$^5$ .................... C08B 37/16; A61K 31/715; A61K 31/445
[52] U.S. Cl. ..................................... 514/58; 536/103; 514/315; 514/869
[58] Field of Search ..................... 514/58, 315, 869; 536/103

[56] References Cited

U.S. PATENT DOCUMENTS 4,834,985  5/1989  Elger et al. ..................... 424/488

OTHER PUBLICATIONS

Advances in Prostaglandins, Thromboxane and Leukotriene Research, vol. 13, (1985), pp. 131–139, (Patrono et al.).
Prostaglandins and The Kidney, (1983), pp. 399–406, (Foegh et al.).
The Lancet, 29 Aug. 1981, pp. 433 & 434, (Foegh et al.).
J. Clin. Invest., vol. 76, (1985), pp. 1011–1018, (Patrono et al.).
Clinical Research, vol. 35, (1987), pp. 544A (Ciabattoni et al.).
Am. J. Physiol., 233(5), (1977), pp. H573–H579, (Feigen et al.).
Prostaglandins and The Kidney, (1983), pp. 309–317, (Morrison et al.).
Am. J. Physiol., 248, (1985), pp. F753–F756, (Zipser).
Am. J. Med., vol. 80, (1986), pp. 34–45, (Stork et al.).
Prostaglandins and The Kidney, (1983), pp. 263–274, (Zipser et al.).
Am. J. Med., vol. 81, (1986), pp. 71–83, (Patrono et al.).

*Primary Examiner*—Ronald W. Griffin
*Assistant Examiner*—Pamela S. Webber
*Attorney, Agent, or Firm*—Bacon & Thomas

[57] ABSTRACT

The use is described of [1R-[1α(Z),2β,3β,5α]]-(+)-7-[5-[[(1,1'-biphenyl)-4-yl]methoxy]-3-hydroxy-2-(1-piperidinyl)cyclopentyl]-4-heptenoic acid or a physiologically acceptable salt, solvate or cyclodextrin complex thereof in the manufacture of medicaments for the therapy or prophylaxis of chronic glomerular diseases including glomerulonephritis, lupus nephritis and systemic lupus erythematosus, renal failure, renal hypertension, hepatorenal syndrome, proteinurea (e.g. albuminurea and microalbuminurea), haemolytic uraemic syndrome and renal impairment following ureteral obstruction.

5 Claims, No Drawings

USE OF A THROMBOXANE RECEPTOR ANTAGONIST IN RENAL DISEASES AND DYSFUNCTION

This invention relates to a new medical use for [1R-[1α(Z),2β,3β,5α]]-(+)-7-[5-[[(1,1'-biphenyl)-4-yl]methoxy]-3-Rydroxy-2-(1-piperidinyl)cyclopentyl]-4-heptenoic acid (hereinafter referred to as Compound A) or a physiologically acceptable salt, solvate or cyclodextrin complex thereof. In particular, it relates to the use of Compound A or a physiologically acceptable salt, solvate or cyclodextrin complex thereof in the therapy or prophylaxis of certain renal diseases and renal dysfunction.

Our UK Patent Specification 2097397 describes inter alia Compound A which is a potent thromboxane receptor blocker. We have stated therein that the compounds of the invention, including Compound A, inhibit thromboxane $A_2$ and endoperoxide mediated aggregation of blood platelets and contraction of vascular smooth muscle and are thus of particular interest as anti-thrombotic agents.

We have now found that Compound A or a physiologically acceptable salt, solvate or cyclodextrin complex thereof is of use in the therapy or prophylaxis of certain renal diseases and renal dysfunction. More particularly, Compound A or a physiologically acceptable salt, solvate or cyclodextrin complex thereof is useful in the therapy or prophylaxis of chronic glomerular diseases including glomerulonephritis, lupus nephritis and systemic lupus erythematosus, renal failure, renal hypertension, hepatorenal syndrome, proteinurea (e.g. albuminurea and microalbuminurea), haemolytic uraemic syndromes and renal impairment following ureteral obstruction. It is to be understood that a reference herein to 'renal disease' is a reference to, and only to, the aforementioned specific disease states.

Thus, according to one aspect of the present invention, we provide Compound A or a physiologically acceptable salt, solvate or cyclodextrin complex thereof for use in the manufacture of a medicament for the therapy or prophylaxis of renal disease in a human or animal subject.

It is preferable to employ Compound A or a physiologically acceptable salt, solvate or cyclodextrin complex thereof in the form of a formulation. The present invention therefore also provides a composition for use in combatting renal disease comprising Compound A or a physiologically acceptable salt, solvate or cyclodextrin complex thereof together, where desirable, with one or more carriers or excipients.

In a further aspect of the invention, we provide a method of treatment of a human or animal subject for combatting renal disease by therapy or prophylaxis which method comprises administering to the said subject an effective amount of Compound A or a physiologically acceptable salt, solvate or cyclodextrin complex thereof.

Compound A or a physiologically acceptable salt, solvate or cyclodextrin complex thereof may be used according to the present invention in various formulations for oral or parenteral administration. Suitable formulations for use according to the present invention are described in GB-B-2097397, GB-B-2127406 and UK Patent Application No. 8829793.

Suitable salts of Compound A include acid addition salts derived from inorganic and organic acids such as hydrochlorides, hyrobromides, sulphates, phosphates, maleates, tartrates, citrates, benzoates, 2-chlorobenzoates, p-toluenesulphonates, methanesulphonates, salicylates, fumarates, lactates, hydroxynaphthalenecarboxylates (e.g. 1-hydroxy- or 3-hydroxy-2-naphthalenecarboxylates) or furoates, or salts with suitable bases such as alkali metal (e.g. sodium and potassium), alkaline earth metal (e.g. calcium or magnesium), ammonium and substituted ammonium (e.g. dimethylammonium, triethylammonium, 2-hydroxyethyl dimethylammonium, piperazine, N,N-dimethylpiperazine, piperidine, ethylenediamine and choline) salts. A preferred salt of Compound A is the hydrochloride salt. Compound A and physiologically acceptable salts and solvates thereof are described in GB-B-2097397 and GB-B-2127406.

When Compound A is used according to the present invention in the form of a cyclodextrin complex, the complex conveniently contains a molar ratio of Compound A with cyclodextrin within the range 1:1 to 1:3.

The term "cyclodextrin" means herein an unsubstituted or substituted α-, β- or γ-cyclodextrin (or a hydrate thereof) or a mixture of two or three of them. Examples of suitable substituted cyclodextrins include sulphur-containing cyclodextrins, nitrogen-containing cyclodextrins, alkylated (e.g. methylated) cyclodextrins such as mono-, di- or trimethylated derivatives of a cyclodextrin (e.g. of β-cyclodextrin) and hydroxyalkyl (e.g. hydroxypropyl) cyclodextrins such as hydroxypropyl β-cyclodextrin and acylated derivatives thereof. Hydroxyalkyl (e.g. hydroxypropyl) cyclodextrins such as hydroxypropyl β-cyclodextrin have been found to be particularly suitable.

A particularly preferred cyclodextrin complex of Compound A is the β-cyclodextrin complex in which the molar ratio of Compound A with β-cyclodextrin is about 1:1.

Cyclodextrin complexes of Compound A and pharmaceutical formulations containing them are described in our co-pending British Patent Application No. 8829793. The cyclodextrin complexes may be prepared by mixing Compound A or the hydrochloride salt thereof with the cyclodextrin in a suitable solvent such as water or an organic solvent which is miscible with water (e.g. an alcohol such as methanol). The reaction may take place at any temperature in the range from 0° to 80° C. However, the mixture is preferably kept at around room temperature and the desired complex obtained by concentrating the mixture under reduced pressure or by allowing the mixture to cool. The mixing ratio of organic solvent with water may be suitably varied according to the solubilities of the starting materials and products. Preferably 1 to 4 moles of cyclodextrin are used for each mole of Compound A or its hydrochloride salt.

Pharmaceutical formulations containing a cyclodextrin complex of Compound A may be prepared in conventional manner by mixing the complex with one or more pharmaceutical carriers or excipients, for example, according to the general methods described in GB-B-2097397 and GB-B-2127406.

When Compound A or a physiologically acceptable salt, solvate or cyclodextrin complex is to be administered as an aqueous formulation for, in particular, parenteral (e.g. intravenous) use, the composition may be prepared according to the general methods described in GB-B-2097397 and GB-B-2127406. Alternatively, the aqueous compositions may be prepared by mixing Compound A or, more preferably, the hydrochloride salt thereof with cyclodextrin together with one or more pharmaceutical carriers or excipients, for example as described in the Examples hereinafter. Preferably, Compound A or its hydrochloride salt are dissolved in water and the remaining constituents are added thereto.

The molar ratio of Compound A or its hydrochloride salt with cyclodextrin in the aqueous composition is conveniently within the range 1:1 to 1:3.

Preferably, the aqueous formulation comprises the hydrochloride salt of Compound A and β-cyclodextrin (or a hydrate thereof) at about physiological pH wherein the formulation contains at least about 1.2 moles of β-cyclodextrin (e.g. 1.2 to 2 moles) for every one mole of the hydrochloride salt of Compound A. Preferably the molar ratio will be about 1:1.4 (e.g. 1:1.28).

The precise dose of Compound A or a physiologically acceptable salt, solvate or cyclodextrin complex thereof to be administered will, of course, depend on a number of factors including, for example, the age and weight of the patient and the route of administration. An effective oral dose, however, in the case of Compound A or a physiologically acceptable salt, solvate or cyclodextrin complex thereof is likely to be in the range from 0.05 to 20 mg/kg body weight of patient per day, preferably in the range from 0.05 to 5 mg/kg per day.

The concentration of Compound A or the hydrochloride salt thereof in the aforementioned aqueous formulations suitable for parenteral administration, in particular for administration by injection (eg intravenously), is conveniently within the range 0.1-10 mg/ml, e.g. 0.1-5 mg/ml, expressed as the free base. Preferably, the concentration is 2 mg/ml expressed as the free base when the aqueous formulation is administered by intravenous injection. If desired, a higher concentration may be used and the solution may be diluted prior to use with, for example, an isotonic saline solution or dextrose or mannitol solution. Conveniently, solutions suitable for injection are presented in an appropriate dose volume (eg 1-100 ml). Dilutions suitable for continuous infusion may have a concentration of Compound A or its hydrochloride salt of 0.01-0.2 mg/ml expressed as the free base. The solution for continuous infusion may be presented in this form, for example in packs of 50-100 ml, or may be presented in more concentrated forms for subsequent dilution before use with, for example, an isotonic saline solution or dextrose or mannitol solution. Alternatively, small volumes of a more concentrated solution (eg 0.1-5 mg/ml) may be utilised for continuous infusion conveniently administered at a rate of 0.5 to 9.9 ml/h.

The aforementioned aqueous formulations may also be adapted for oral administration (e.g. as a capsule, syrup or solution). The preparation of suitable formulations for oral use will be within the knowledge of persons skilled in the art and may generally follow the procedures described in GB-B-2097397, GB-B-2127406 and in the Examples hereinafter.

The following examples are provided in illustration of the present invention and should not be construed in any way as constituting a limitation thereof.

PHARMACEUTICAL EXAMPLES OF PARENTERAL INJECTIONS/INFUSIONS COMPRISING THE HYDROCHLORIDE SALT OF COMPOUND A

| (i) Hydrochloride salt of Compound A equivalent to 50 mg base | | | |
|---|---|---|---|
| β-Cyclodextrin hydrate | 143 mg | 166 mg | 238 mg |
| Sodium hydroxide solution | to pH 7 | to pH 7 | to pH 7 |
| Water suitable for injection | to 50 ml | to 50 ml | to 50 ml |

The hydrochloride salt of Compound A was dissolved in 35 ml water suitable for injection and the β-cyclodextrin was added. This solution was titrated to pH 7 with 0.02M sodium hydroxide solution and then adjusted to volume with water suitable for injection.

The solution may then be sterilised by filtration and filled into vials or ampoules.

| (ii) Hydrochloride salt of Compound A equivalent to 50 mg base | |
|---|---|
| β-Cyclodextrin hydrate | 166 mg |
| Sodium chloride | 450 mg |
| pH 7.0 phosphate buffer | 2.5 ml |
| Sodium hydroxide solution | to pH 7 |
| Water suitable For injection | to 50 ml |

The hydrochloride salt of Compound A was dissolved in approximately 25 ml water suitable for injection. The β-cyclodextrin was dissolved therein and the resulting solution was titrated to pH 6 with 0.02M sodium hydroxide solution and the phosphate buffer added. The sodium chloride was added to the solution and the pH adjusted to pH 7 with sodium hydroxide. The solution was made up to volume with water suitable for injection. A sample of this solution was filled into a glass vial which was sealed with a rubber plug and metal overseal. This was then autoclaved.

| (iii) Hydrochloride salt of Compound A equivalent to 50 mg base | |
|---|---|
| Hydroxyproply-β-cyclodextrin | 170 mg |
| Mannitol | 2.5 g |
| pH 6.0 phosphate buffer | 5.0 ml |
| Sodium hydroxide solution | to pH 6 |
| Water suitable for injection | to 50 ml |

The hydrochloride salt of Compound A was dissolved in approximately 25 ml water suitable for injection and the hydroxypropyl-β-cyclodextrin was added. The mannitol was then added and the solution titrated to pH 6 with 0.02M sodium hydroxide solution. The phosphate buffer solution was added and the solution adjusted to volume with water suitable for injection. The solution was then filtered and filled into glass vials which were sealed with rubber plugs and metal overseals. These were then autoclaved.

| (iv) Hydrochloride salt of Compound A equivalent to 50 mg base | |
|---|---|
| β-Cyclodextrin hydrate | 166 mg |
| Mannitol | 2.5 g |
| Sodium acid phosphate | 46 mg |
| Disodium phospate, anhydrous | 5 mg |
| Sodium hydroxide solution | to pH 6 |

| -continued | |
|---|---|
| Water suitable for injection | to 50 ml |

The hydrochloride salt of Compound A was dissolved in approximately 25 ml water suitable for injection. The β-cyclodextrin and mannitol were dissolved therein and the solution titrated to pH 6 with 0.02M sodium hydroxide solution. The sodium acid phosphate and anhydrous disodium phosphate were dissolved in water suitable for injection. This solution was added to the bulk solution which was made up to volume with water suitable for injection. The solution was filtered and filled into glass ampoules which were sealed and then autoclaved.

| | Cyclodextrin | | | |
|---|---|---|---|---|
| | | | Mixture | |
| | α | γ | β | + γ |
| (v) Hydrochloride salt of Compound A equivalent to 50 mg base | | | | |
| Cyclodextrin | 143 mg | 190 mg | 119 mg | 136 mg |
| Mannitol | 2.5 g | 2.5 g | 2.5 g | |
| pH 6.0 Phosphate buffer | 5.0 ml | 5.0 ml | 5.0 ml | |
| Sodium hydroxide solution | to pH 6 | to pH 6 | to pH 6 | |
| Water suitable For injection injection | to 50 ml | to 50 ml | to 50 ml | |

The hydrochloride salt of Compound A was dissolved in approximately 25 ml water suitable for injection and the cyclodextrin(s) was (were) added. The mannitol was then added and the solution titrated to pH 6 with 0.02M sodium hydroxide solution. The phosphate buffer solution was added and the solution was adjusted to volume with water suitable for injection. The solution was then filtered and filled into glass vials which were sealed with rubber plugs and metal overseals.

PHARMACEUTICAL EXAMPLE OF AN ORAL SYRUP COMPRISING THE HYDROCHLORIDE SALT OF COMPOUND A

| Hydrochloride salt of Compound A equivalent to 2.5 mg base | |
|---|---|
| β-cyclodextrin hydrate | 9 mg |
| Citric acid | to pH 4.5 |
| Methyl hydroxybenzoate sodium | 5 mg |
| Propyl hydroxybenzoate sodium | 2 mg |
| Liquid orange flavour | qs |
| Sucrose | 3.25 g |
| Purified water | to 5.0 ml |

Dissolve the sucrose in a minimum quantity of water. Add the hydrochloride salt of Compound A and then the β-cyclodextrin with stirring; adjust the pH to 4.5 with citric acid. With continued stirring add a solution of the hydroxybenzoates and lastly the flavour. Adjust almost to volume with water and stir. Check the pH and adjust to 4.5 with citric acid if necessary. Make up to volume with water.

I claim:

1. A method of treatment of a human or animal subject for combatting renal disease by therapy or prophylaxis, which method comprises administering to said subject an effective amount of [1R-[1α(Z),2β,3β,5α]]-(+)-7-[5-[[(1,1'-biphenyl)-4-yl]methoxy]-3-hydroxy-2-(1-piperidinyl) cyclopentyl]-4-heptenoic acid (Compound A) or a physiologically acceptable salt, solvate or cyclodextrin complex thereof.

2. A method as claimed in claim 1 for the therapy or prophylaxis of chronic glomerular diseases, renal failure, renal hypertension, hepatorenal syndrome, proteinurea, haemolytic uraemic syndromes or renal impairment following ureteral obstruction.

3. A method as claimed in claim 1 in which Compound A is in the form of its hydrochloride salt.

4. A method as claimed in claim 1 in which Compound A or a physiologically acceptable salt, solvate or cyclodextrin complex thereof is presented in a form suitable for oral or parenteral administration.

5. A method as claimed in claim 4 in which Compound A or a physiologically acceptable salt, solvate or cyclodextrin complex thereof is presented in an amount sufficient to administer 0.05 to 20 mg/kg body weight per day to said subject.

* * * * *